(12) United States Patent
Rosero et al.

(10) Patent No.: US 11,460,721 B2
(45) Date of Patent: Oct. 4, 2022

(54) ILLUMINATED EYEWEAR DEVICE

(71) Applicant: DESIGN LED PRODUCTS LIMITED, West Lothian (GB)

(72) Inventors: Adám Rosero, West Lothian (GB); James Gourlay, West Lothian (GB)

(73) Assignee: Design Led Products Limited, Lothian (GB)

( * ) Notice: Subject to any disclaimer, the term of this patent is extended or adjusted under 35 U.S.C. 154(b) by 710 days.

(21) Appl. No.: 16/335,800

(22) PCT Filed: Sep. 26, 2017

(86) PCT No.: PCT/GB2017/052874
§ 371 (c)(1),
(2) Date: Mar. 22, 2019

(87) PCT Pub. No.: WO2018/055418
PCT Pub. Date: Mar. 29, 2018

(65) Prior Publication Data
US 2020/0026101 A1   Jan. 23, 2020

(30) Foreign Application Priority Data
Sep. 26, 2016 (GB) ..................... 1616318

(51) Int. Cl.
*G02C 11/04* (2006.01)
*A61N 5/06* (2006.01)
(Continued)

(52) U.S. Cl.
CPC ............ *G02C 11/04* (2013.01); *A61N 5/0618* (2013.01); *A61M 2021/0044* (2013.01);
(Continued)

(58) Field of Classification Search
CPC ...... G02C 11/04; G02C 7/086; A61N 5/0618; A61N 2005/0648; A61N 2005/0652;
(Continued)

(56) References Cited

U.S. PATENT DOCUMENTS

| 8,189,263 B1 | 5/2012 | Wang et al. |
| 8,508,830 B1 * | 8/2013 | Wang ................. G02B 27/0172 359/267 |

(Continued)

FOREIGN PATENT DOCUMENTS

| GB | 2313550 A | 2/2000 |
| WO | WO2003/008860 A1 | 1/2003 |

(Continued)

*Primary Examiner* — Evan P Dzierzynski
(74) *Attorney, Agent, or Firm* — FisherBroyles, LLP

(57) ABSTRACT

An illuminated eyewear device is described. The illuminated eyewear device comprises a transparent substrate and one or more light sources mounted around the perimeter of the transparent substrate. The output of the one or more light sources is arranged to be coupled into, and propagates within, the transparent substrate. Applied to an inner surface of the transparent substrate are a plurality of refractive light scattering means designed to break the condition for total internal reflection of the light generated by the one or more light sources. As well as being mobile, compact and easy to integrate into everyday life, the above described illuminated eyewear device address the known problem of glare experienced by users of those devices known in the art since the light sources are not directly imaged into the user eye.

21 Claims, 3 Drawing Sheets

(51) Int. Cl.
*F21Y 115/10* (2016.01)
*A61M 21/00* (2006.01)

(52) U.S. Cl.
CPC ............... *A61N 2005/0648* (2013.01); *A61N 2005/0652* (2013.01); *A61N 2005/0666* (2013.01); *F21Y 2115/10* (2016.08)

(58) Field of Classification Search
CPC ... A61N 2005/0666; A61N 2005/0651; A61M 2021/0044; F21Y 2115/10; G02B 27/0172; G02B 2027/0178
See application file for complete search history.

(56) References Cited

U.S. PATENT DOCUMENTS

| 8,582,209 | B1* | 11/2013 | Amirparviz | G02B 27/147 |
| | | | | 359/630 |
| 8,743,464 | B1* | 6/2014 | Amirparviz | G02B 27/0172 |
| | | | | 359/633 |
| 9,097,891 | B2* | 8/2015 | Border | G02B 27/017 |
| 2001/0053075 | A1 | 12/2001 | Parker et al. | |
| 2009/0141324 | A1* | 6/2009 | Mukawa | G02B 5/1814 |
| | | | | 359/13 |
| 2010/0171680 | A1* | 7/2010 | Lapidot | G02B 27/0172 |
| | | | | 345/8 |
| 2010/0182801 | A1* | 7/2010 | Ye | G02B 6/0043 |
| | | | | 362/623 |
| 2013/0201723 | A1 | 8/2013 | Gourlay | |
| 2015/0167926 | A1* | 6/2015 | Yu | F21K 9/90 |
| | | | | 362/311.02 |
| 2015/0182759 | A1 | 7/2015 | Baek et al. | |
| 2015/0241707 | A1 | 8/2015 | Schowengerdt | |
| 2015/0370075 | A1 | 12/2015 | Ato et al. | |
| 2016/0016004 | A1 | 1/2016 | Hudson | |
| 2016/0238843 | A1 | 8/2016 | Dobschal et al. | |
| 2016/0284674 | A1* | 9/2016 | Kim | H01L 25/0753 |

FOREIGN PATENT DOCUMENTS

| WO | WO2012/025398 A1 | 3/2012 |
| WO | WO2013/057242 A1 | 4/2013 |

\* cited by examiner

ILLUMINATED EYEWEAR DEVICE

This application is the U.S. National Stage of International Application No. PCT/GB2017/052874, which was filed on Mar. 26, 2017. This application also claims the benefit of the filing date of GB patent application No. 1616318.0, which was filed on Sep. 26, 2016. The contents of both of those applications are hereby incorporated by reference.

The present invention relates to the field of lighting and in particular to eyewear that incorporates a light source. The invention is suitable for a range of applications, particularly, use in the treatment of light related medical conditions.

BACKGROUND TO THE INVENTION

Light plays a role in the well-being of a person. For example, in countries with a significant seasonal variation in sunlight the population may be more prone to Seasonal Affective Disorder (SAD). This is a type of mental depression with the symptoms typically being found to be more severe in the winter months.

A possible treatment for people with SAD is light therapy. Light therapy can also help people with workplace stress, skin conditions and use within clinical trials to monitor physiological effects of light on humans. In practice, light therapy has involved exposing a person to a bright light box, at an exact distance from the user, for a sustained period of time. Such an arrangement can obviously be difficult to incorporate into a normal daily routine.

More recently, wearable products have become available on the market as an alternative to the cumbersome light box have e.g. The Luminette® by Lucimed. These products exploit the development of miniature electronic components. It will be appreciated by those skilled in the art that the integration of electronic components to compact wearable products is not a straightforward process and thus involves significant increases in the complexity of the production process for these devices.

FIG. 1 presents a cross-sectional view of a prior art illuminated eyewear device 1. This device 1 comprises a frame 2 which rests across the forehead of a user. Attached to the frame are two arms 3 extending either side of the user's face and a nose support 4, which together hold the device 1 in situ on a user's face. Mounted to the frame 2 is a light source 5 and screen 6. Light 7 from the light source 5 is reflected off the screen 6 into the user's eye 8. The user's eye lens 9 focuses the light 7 following reflection from the screen 6 onto the user's eye retina 10.

A known problem with such illuminated eyewear devices is that they tend to produce optical glare which acts as a source of discomfort for the user.

It is an object of an aspect of the present invention to provide an illuminated eyewear device that obviates or at least mitigates one or more of the aforesaid disadvantages.

SUMMARY OF THE INVENTION

According to a first aspect of the present invention there is provided an illuminated eyewear device comprising a transparent substrate having a first outer surface and a second inner surface and one or more light sources mounted around the perimeter of the transparent substrate, the output of the one or more light sources is coupled into, and propagates within, the transparent substrate, wherein the transparent substrate further comprises a plurality of refractive light scattering elements located within the transparent substrate or upon the second inner surface that provide a means to redirect the light out of, and away from, the transparent substrate via the second inner surface.

As well as being mobile, compact and easy to integrate into everyday life, the above described illuminated eyewear device address the known problem of glare experienced by users of those devices known in the art since the light sources are not directly imaged into the user eye. This arrangement also has the advantage of the user viewing a diffuse continuum of light emanating from the entire spatial extent of the transparent substrate.

Optionally, the one or more light sources emit a single wavelength of visible light. Alternatively, the one or more light sources emit different visible wavelengths of light.

Most preferably, the transparent substrate comprises glass or a transparent polymer, such as acrylic, Poly(methyl methacrylate) (PMMA), polycarbonate, silicone or polyurethane.

Most preferably the plurality of refractive light scattering elements comprise a transparent or translucent material having a refractive index that is equal to, or greater than, a refractive index of the transparent substrate. The refractive light scattering elements may comprise one or more light scattering means selected from a group comprising a microlenses, white or coloured ink dots or patterns, patterns or layers of colour changing materials, such as photoluminescent, quantum dots or nano-materials.

Preferably the plurality of refractive light scattering elements comprise an irregular matrix of refractive light scattering elements. The irregular array may comprise refractive light scattering elements of varying area and or varying separation. An advantage of varying the area and or separation, or equivalent parameters, in the refractive surface scattering layer is a uniform intensity distribution across the extent of the transparent substrate can be achieved Alternatively, the plurality of refractive elements comprise a regular matrix of refractive elements.

The transparent substrate may comprise a wedge of have a tapered profile such that a thickness of the transparent substrate is reduced as light propagates away from the one or more light sources. This provides an alternative arrangement for enabling light to escape across the transparent substrate surface.

Preferably, the illuminated eyewear device further comprises a control unit that provide a means to independently control the intensity of the one or more light sources.

Preferably, the one or more light sources are LEDs.

Preferably the illuminated eyewear device further comprises a wireless transmitter and receiver that provides a means to transmit and or receive control instructions and data to and from an external device.

Optionally, the transparent substrate further comprises a corrective lens layer.

Optionally, the transparent substrate comprising a light scattering means is a single piece of moulded polymer.

According to a second aspect of the present invention there is provided a method of producing an illuminated eyewear device the method comprising
   providing a transparent substrate having a first outer surface and a second inner surface;
   mounting one or more light sources around the perimeter of the transparent substrate, the output of the one or more light sources is coupled into, and propagates within, the transparent substrate;
   providing the transparent substrate with a plurality of refractive light scattering elements located within the transparent substrate or upon the second inner surface that provide a means to redirect the light out of, and away from, the transparent substrate via the second inner surface.

Optionally, the application of the light scattering means comprises etching a patterned layer.

Alternatively, the application of the light scattering means comprises printing a patterned, refractive ink layer.

Alternatively, the application of the light scattering means comprises 3d printing a patterned layer.

Alternatively, the application of the light scattering means comprises applying a resin layer containing particulates.

Embodiments of the second aspect of the invention may comprise features to implement the preferred or optional features of the first aspect of the invention or vice versa.

BRIEF DESCRIPTION OF DRAWINGS

There will now be described, by way of example only, various embodiments of the invention with reference to the drawings, of which.

Figure 1:
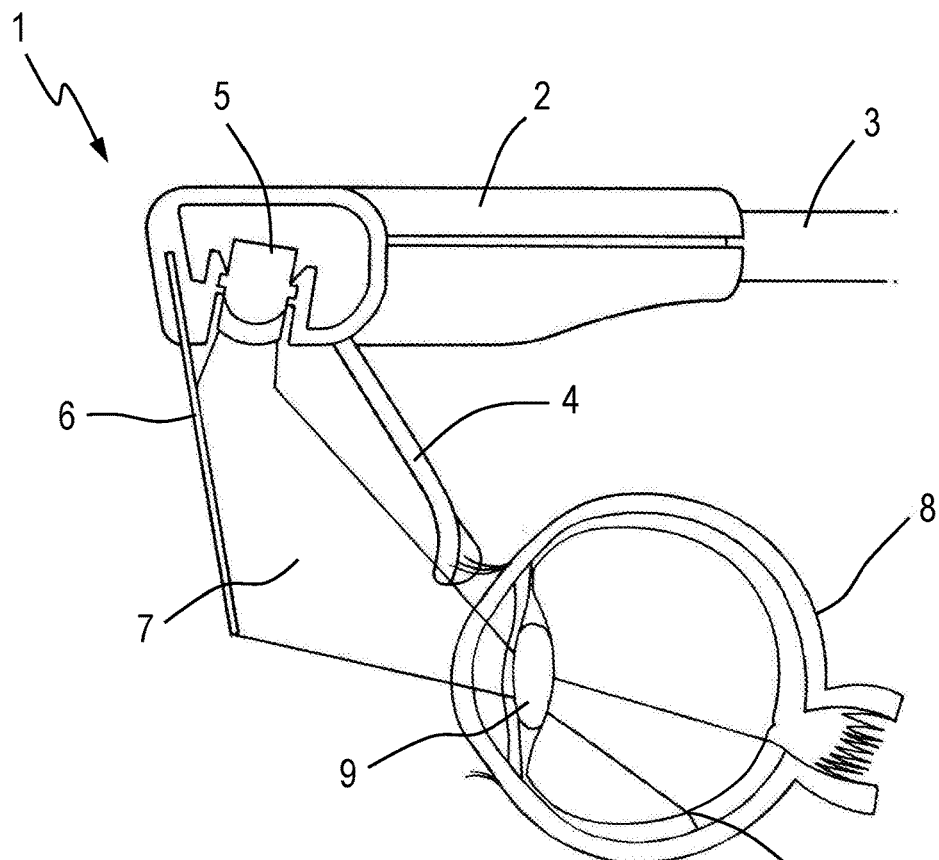
FIG. 1 presents a cross-sectional side view of a prior art illuminated eyewear device.

In the description which follows, like parts are marked throughout the specification and drawings with the same reference numerals. The drawings are not necessarily to scale and the proportions of certain parts have been exaggerated to better illustrate details and features of embodiments of the invention.

The term transparent in the context of the following description of the illuminated eyewear device means transmissive within the normal visible region of the electromagnetic spectrum e.g. 390 nm to 700 nm.

DETAILED DESCRIPTION OF THE PREFERRED EMBODIMENTS

Figure 2:
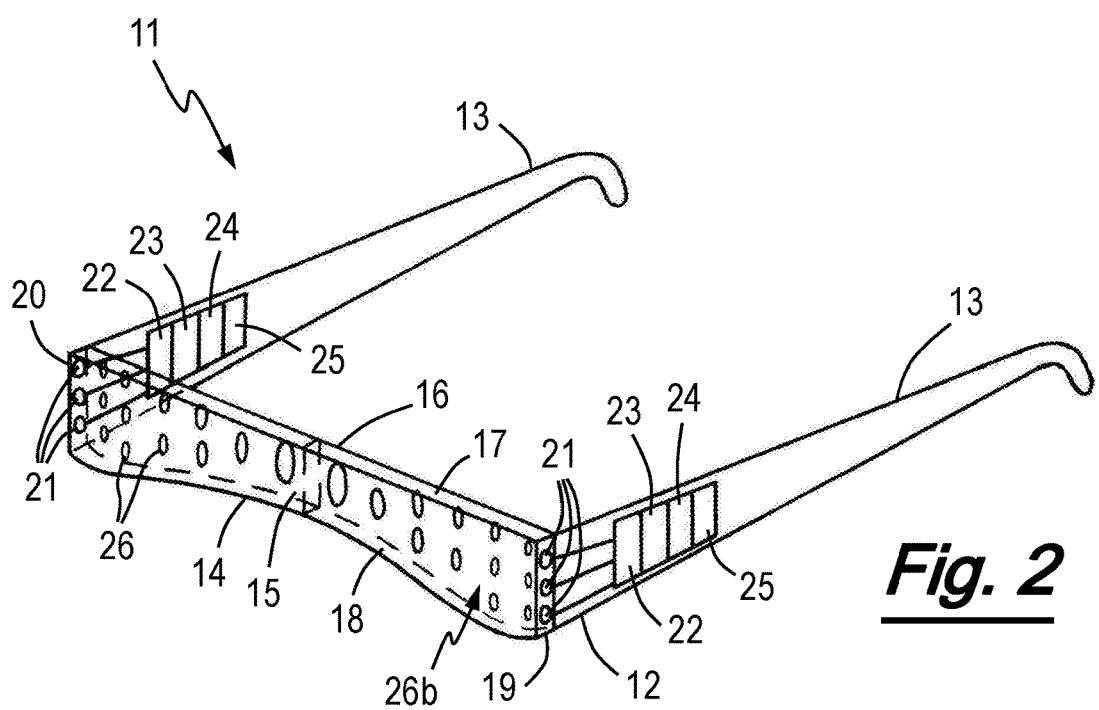
FIG. 2 presents a perspective view of an illuminated eyewear device in accordance with an embodiment of the present invention.
Figure 3:
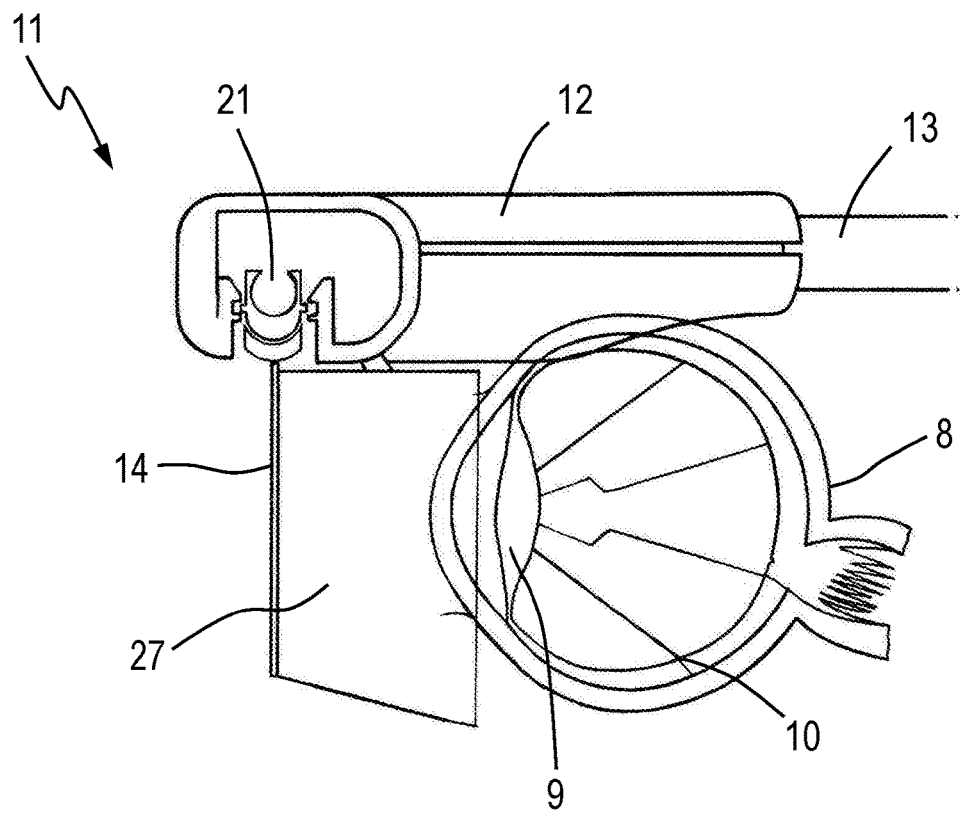
FIG. 3 presents a cross-sectional side view of an alternative embodiment of the illuminated eyewear device.
Figure 4:
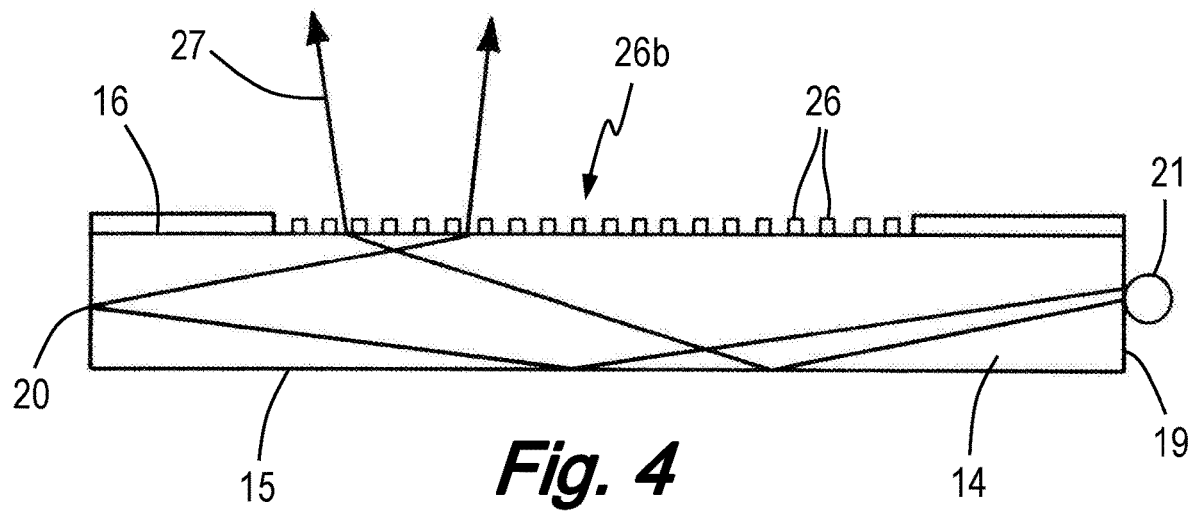
FIG. 4 presents a cross-sectional top view of a light guide component of the illuminated eyewear device of FIG. 2.
Figure 5:
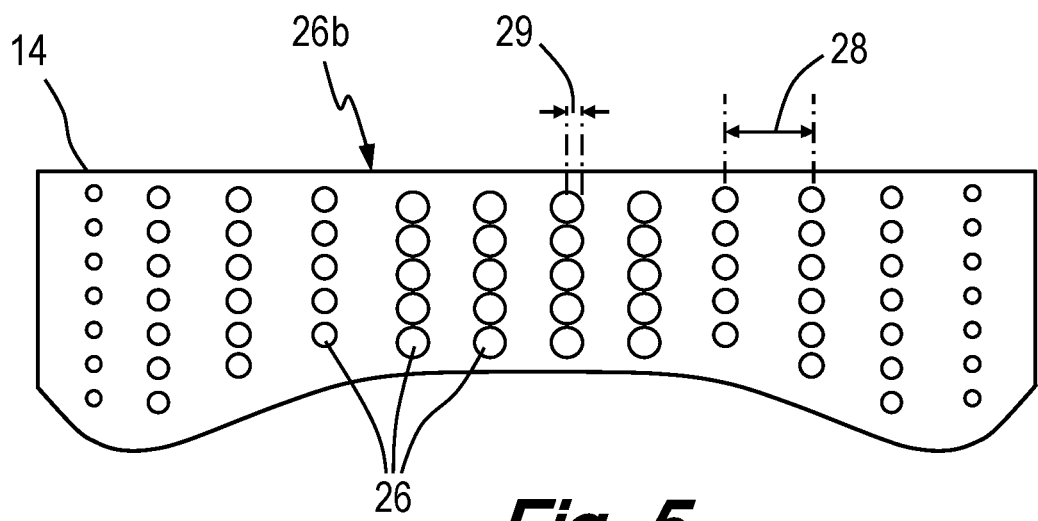
FIG. 5 presents a front view of the light guide component of the illuminated eyewear device of FIG. 2.
Figure 6:
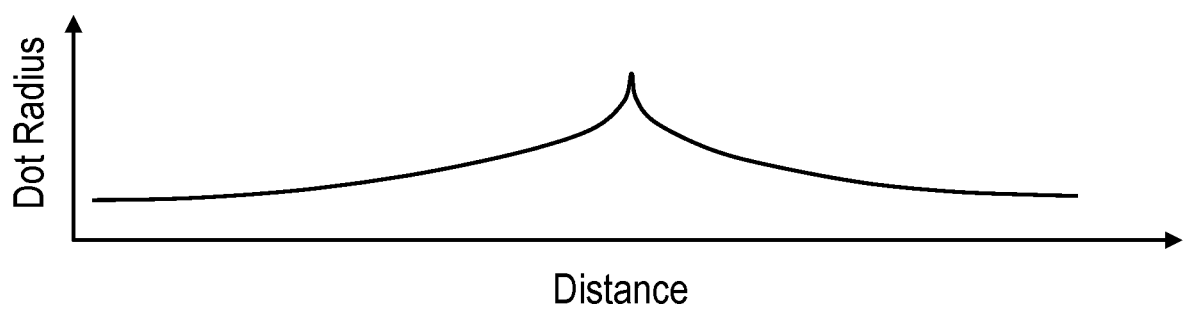
FIG. 6 presents a plot of dot radius as a function of distance along the front surface of the light guide component of the illuminated eyewear device of FIG. 2.

An explanation of the present invention will now be described with reference to FIGS. 2 to 6. In particular, FIG. 2 presents a perspective view of an illuminated eyewear device 11 in accordance with an embodiment of the present invention, while FIG. 3 provides a cross-sectional side view of this device 11. FIGS. 4 to 6 illustrate various components of the illuminated eyewear device 11 of FIG. 2.

It can be seen that the illuminated eyewear device 11 comprising a frame 12 mounted to which are two arms 13 that during use extend either side of a user's face.

A transparent substrate 14 is also mounted to the frame 12. The transparent substrate 14 has an opposing first outer surface 15 and a second inner surfaces 16 (defined relative to the user of the illuminated eyewear device 11), and a number of edges 17, 18, 19, and 20 extending between the first outer surface 15 and the second inner surface 16. The transparent substrate 14 may comprise glass or a transparent polymer, such as acrylic, Poly(methyl methacrylate) (PMMA), polycarbonate, silicone or polyurethane.

Mounted at edges 19 and 20 of the transparent substrate 14 are three light sources 21 in the form of LEDs. The transparent substrate 14 is therefore illuminated by light emitted from the edge mounted LEDs 21. In the presently described embodiment the light sources 21 comprise a single colour e.g. blue light ~470 nm. Other colours within the visible region of the electromagnetic spectrum may alternatively be employed.

The LEDs 21 are connected to a power supply 22, a control unit 23, a wireless transmitter and receiver 24, and control inputs 25 mounted to the frame 12. These electronic components 22, 23, 24, 25 are employed to power and control the operation of the illuminated eyewear device 11.

The control unit 23 can independently control the intensity and or viewed colour of the one or more of the LEDs 21.

The wireless transmitter and receiver 24 can facilitate receiving control instructions from an external device such as a mobile phone. Furthermore, the wireless component 24 can transmit usage data to an external device which will record, monitor and process this data.

Also, the wireless component 24 could pair the illuminated eyewear device 11 to other illuminated eyewear devices 11 so as to run synchronised illumination programs.

The control inputs 25 mounted to the frame 12 may take the form of, for example, an on and off button for the entire illuminated eyewear device 11 or a variable input wheel to control the global intensity of all the LEDs 21.

The transparent substrate 14 is arranged to internally reflect light generated by the one or more light sources 21. The transparent substrate 14 therefore acts as a light guide. Applied to the second inner surface 16 of the transparent substrate 14 are a plurality of refractive light scattering means 26 designed to break the condition for total internal reflection of the light generated by the one or more light sources. In other words, the light scattering means 26 uses refractive optics to redirect the light propagating within the transparent substrate 14 to exit the transparent substrate 14 via the second inner surface 16 i.e. into the eye of a user of the illuminated eyewear device 11.

In the presently described embodiment the refractive light scattering means 26 takes the form of a matrix of refractive elements 26b. Preferably the matrix of refractive elements 26b comprises an irregular matrix of refractive elements 26. The refractive elements 26 preferably comprise a transparent or translucent material having a refractive index that is equal to, or greater than, the refractive index of the transparent substrate 14. The combined effects of the refractive elements 26 is to therefore provide the means for redirecting the light propagating within the transparent substrate 14 out of the transparent substrate 14 via the second inner surface 16.

The refractive elements 26, can be applied using a number of techniques known to those skilled in the art such as etching, printing, 3d printing or applying a resin containing particulates. It will be appreciated that the transparent substrate 14 comprising a refractive light scattering means 26 may comprise a single piece of moulded polymer.

As can be seen from FIG. 2, the edge 18 of the transparent substrate 14 is curved, to provide an ergonomically shaped nose support for supporting the illuminated eyewear device 11 on a user.

FIG. 3 presents a cross-sectional side view of the illuminated eyewear device 11 respectively. In the embodiment presented in FIG. 3 the LED light sources 21 are mounted along edge 17 of the transparent substrate 14 as opposed to the edges 19 and 20 as depicted in the embodiment of FIG. 2.

FIG. 4 presents a cross-section top view of the transparent substrate 14 of FIG. 2.

The direction of propagation of the light emitted from the light sources 21 is clearly illustrated by FIG. 3 and FIG. 4. Following propagation through the transparent substrate 14 the light 27 is redirected by the refractive elements 26 to emanate from the entire second inner surface 16 of the transparent substrate 14. The illuminated eyewear device 11 effectively provides multiple light sources or a continuum of light sources, on the second inner surface 16 of the transparent substrate 14 that are imaged on user's retina. Significantly this light 27 is provided as a non-glare, diffuse continuum light source.

As clearly seen in FIG. 5, which presents a front view of the transparent substrate 14, the matrix of refractive elements 26b can be seen to comprise dots. The matrix of refractive elements 26b can therefore be characterised by the separation of the refractive elements 26 i.e. a dot separation 28 and or the area of the refractive elements 26 i.e. the dot radius 29. To achieve a uniform intensity distribution of light 27 across the extent of the transparent substrate 14 the dot separation and or dot radius can both be optimised across the matrix of refractive elements 26b depending on the proximity to a light source 21. More specifically, to compensate for the reduction of light intensity with increasing distance from an LED 21, the dot radius 29 can be increased, as further illustrated by the plot presented by FIG. 6. In other words, the matrix of refractive elements 26b may not be uniform and may even comprise a random distribution of dots to avoid visible optical artefacts.

A lens layer may also be incorporated with the transparent substrate 14 to allow a user requiring prescription glasses to also use the illuminated eyewear device 11.

It will be appreciated by the skilled reader that the above described embodiments are not limited to use of three LEDs at edges 19 and 20, and that more or less light sources 21 may be employed. In addition, the light sources 21 are not limited to deployment with edges 19 and 20 but may alternatively be mounted anywhere around the perimeter of the transparent substrate 14 e.g. on edges 17, 18, 19 and 20. In addition, the light sources may comprise a combination of colours.

In a yet further alternative embodiment the refractive elements 26 may consist of squares instead of circles and be characterised by a dimension of the square or more generically a parameter indicating the fractional area covered.

When optimising the matrix of refractive elements 26b the complexity may increase to incorporate according to factors such as, for example, the addition of a corrective spectacle lens or LEDs 21 positioned across multiple edges.

It will also be appreciated that the refractive scattering means 26 may take alternative forms e.g. microlenses of varying size or pitch, white or coloured ink dots or patterns, patterns or layers of colour changing materials, such as photoluminescent, quantum dots or nano-materials. In addition, scattering means can be applied to the first surface 15, both the first 15 and second 16 surfaces, or within the transparent substrate 14.

In addition, the transparent substrate 14 may be configured as a wedge, with a widening thickness at the light source 21 and the thickness tapering to a reduced thickness away from the light source 21, enabling light to escape across the transparent substrate 14 surface.

As well as being mobile, compact and easy to integrate into everyday life, the above described illuminated eyewear device address the known problem of glare experienced by users of those devices known in the art.

An illuminated eyewear device is described. The illuminated eyewear device comprises a transparent substrate and one or more light sources mounted around the perimeter of the transparent substrate. The output of the one or more light sources is arranged to be coupled into, and propagates within, the transparent substrate. Applied to an inner surface of the transparent substrate are a plurality of refractive light scattering means designed to break the condition for total internal reflection of the light generated by the one or more light sources. As well as being mobile, compact and easy to integrate into everyday life, the above described illuminated eyewear device address the known problem of glare experienced by users of those devices known in the art since the light sources are not directly imaged into the user eye.

The foregoing description of the invention has been presented for purposes of illustration and description and is not intended to be exhaustive or to limit the invention to the precise form disclosed. The described embodiments were chosen and described in order to best explain the principles of the invention and its practical application to thereby enable others skilled in the art to best utilise the invention in various embodiments and with various modifications as are suited to the particular use contemplated. Therefore, further modifications or improvements may be incorporated without departing from the scope of the invention as defined by the appended claims.

The invention claimed is:

1. An illuminated eyewear device comprising a transparent substrate having a first outer surface and a second inner surface and one or more light sources mounted around the perimeter of the transparent substrate, the output of the one or more light sources is coupled into, and propagates within, the transparent substrate,
wherein the transparent substrate further comprises a plurality of refractive light scattering elements located upon the second inner surface that provide a means to redirect the light out of, and away from, the transparent substrate via the second inner surface.

2. An illuminated eyewear device as claimed in claim 1 wherein the one or more light sources emit a single wavelength of visible light.

3. An illuminated eyewear device as claimed in claim 1 wherein the one or more light sources emit different visible wavelengths of light.

4. An illuminated eyewear device as claimed in claim 1 wherein the transparent substrate comprises a glass or a transparent polymer.

5. An illuminated eyewear device as claimed in claim 1 wherein the plurality of refractive light scattering elements comprise a transparent or translucent material having a refractive index that is equal to, or greater than, a refractive index of the transparent substrate.

6. An illuminated eyewear device as claimed in claim 1 wherein the refractive light scattering elements comprise one or more light scattering means selected from a group comprising microlenses, white or coloured ink dots or patterns, patterns or layers of colour changing materials.

7. An illuminated eyewear device as claimed in claim 1 wherein the plurality of refractive light scattering elements comprise an irregular matrix of refractive light scattering elements.

8. An illuminated eyewear device as claimed in claim 7 wherein the irregular array comprises refractive light scattering elements of varying area and or varying separation.

9. An illuminated eyewear device as claimed in claim 1 wherein the plurality of refractive light scattering elements comprise a regular matrix of refractive light scattering elements.

10. An illuminated eyewear device as claimed in claim 1 wherein the transparent substrate comprises a wedge or has a tapered profile wherein a thickness of the transparent substrate is reduced as light propagates away from the one or more light sources.

11. An illuminated eyewear device as claimed in claim 1 wherein the illuminated eyewear device further comprises a control unit that provides a means to independently control the intensity of the one or more light sources.

12. An illuminated eyewear device as claimed in claim 1 wherein the one or more light sources are LEDs.

13. An illuminated eyewear device as claimed in claim 1 wherein the illuminated eyewear device further comprises a wireless transmitter and receiver that provides a means to transmit and or receive control instructions and data to and from an external device.

14. An illuminated eyewear device as claimed in claim 1 wherein the transparent substrate further comprises a corrective lens layer.

15. An illuminated eyewear device as claimed in claim 1 wherein the transparent substrate and light scattering means comprise a single piece of moulded polymer.

16. A method of producing an illuminated eyewear device the method comprising
   providing a transparent substrate having a first outer surface and a second inner surface;
   mounting one or more light sources around the perimeter of the transparent substrate, the output of the one or more light sources is coupled into, and propagates within, the transparent substrate;
   providing the transparent substrate with a plurality of refractive light scattering elements located upon the second inner surface that provide a means to redirect the light out of, and away from, the transparent substrate via the second inner surface.

17. A method of producing an illuminated eyewear device as claimed in claim 16 wherein the application of the light scattering means comprises etching a patterned layer.

18. A method of producing an illuminated eyewear device as claimed in claim 16 wherein the application of the light scattering means comprises printing a patterned, refractive ink layer.

19. A method of producing an illuminated eyewear device as claimed in claim 16 wherein the application of the light scattering means comprises 3d printing a patterned layer.

20. A method of producing an illuminated eyewear device as claimed in claim 16 wherein the application of the light scattering means comprises applying a resin layer containing particulates.

21. An illuminated eyewear device comprising a transparent substrate having a first outer surface and a second inner surface and one or more light sources mounted around the perimeter of the transparent substrate, the output of the one or more light sources is coupled into, and propagates within, the transparent substrate, wherein the transparent substrate further comprises a plurality of refractive light scattering elements located upon the second inner surface of the transparent substrate that provide a means to redirect the light out of, and away from, the transparent substrate via the second inner surface, by breaking the condition for total internal reflection.

* * * * *